(12) United States Patent
Mihajlovic et al.

(10) Patent No.: US 8,696,654 B2
(45) Date of Patent: Apr. 15, 2014

(54) APPARATUS, METHOD AND COMPUTER PROGRAM FOR APPLYING ENERGY TO AN OBJECT

(75) Inventors: Nenad Mihajlovic, Eindhoven (NL); Joachim Kahlert, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 463 days.

(21) Appl. No.: 12/746,198

(22) PCT Filed: Nov. 27, 2008

(86) PCT No.: PCT/IB2008/054984
§ 371 (c)(1),
(2), (4) Date: Jun. 4, 2010

(87) PCT Pub. No.: WO2009/072039
PCT Pub. Date: Jun. 11, 2009

(65) Prior Publication Data
US 2010/0274235 A1    Oct. 28, 2010

(30) Foreign Application Priority Data
Dec. 6, 2007  (EP) .................................. 07122462

(51) Int. Cl.
*A61B 18/18*  (2006.01)
*A61B 19/00*  (2006.01)

(52) U.S. Cl.
USPC .................... 606/16; 606/2; 606/13; 128/898

(58) Field of Classification Search
USPC ........................................ 606/2–19; 128/898
See application file for complete search history.

(56) References Cited

U.S. PATENT DOCUMENTS

| | | | |
|---|---|---|---|
| 5,366,443 A * | 11/1994 | Eggers et al. | 604/114 |
| 5,830,209 A | 11/1998 | Savage et al. | |
| 5,836,946 A | 11/1998 | Diaz et al. | |
| 6,357,447 B1 | 3/2002 | Swanson et al. | |
| 7,087,053 B2 | 8/2006 | Vanney | |
| 2002/0035361 A1* | 3/2002 | Houser et al. | 606/15 |
| 2002/0107511 A1 | 8/2002 | Collins | |
| 2002/0111548 A1 | 8/2002 | Swanson et al. | |
| 2002/0183638 A1 | 12/2002 | Swanson et al. | |
| 2004/0255958 A1* | 12/2004 | Harrington et al. | 128/898 |
| 2005/0119647 A1 | 6/2005 | He et al. | |
| 2006/0264925 A1 | 11/2006 | Sharareh et al. | |
| 2007/0078457 A1 | 4/2007 | Paul et al. | |
| 2007/0100405 A1 | 5/2007 | Thompson | |
| 2009/0005768 A1* | 1/2009 | Sharareh et al. | 606/17 |

FOREIGN PATENT DOCUMENTS

| | | | |
|---|---|---|---|
| WO | 9510318 A1 | 4/1995 | |
| WO | 2005046456 A2 | 5/2005 | |

\* cited by examiner

*Primary Examiner* — Dawayne A Pinkney (57) ABSTRACT

An apparatus for applying energy to an object includes at least one combination element for combining multiple energy applying elements for applying energy to the object. The combination element includes an axis around which the energy applying elements are wound. Further, the energy applying elements include energy emission locations arranged along a line.

18 Claims, 10 Drawing Sheets

APPARATUS, METHOD AND COMPUTER PROGRAM FOR APPLYING ENERGY TO AN OBJECT

CROSS REFERENCE TO RELATED APPLICATIONS

Related applications are IB2008/054965 (Apparatus, Method and Computer Program for Applying Energy to an Object) filed Nov. 26, 2008 and IB2008/055042 (Apparatus, Method and Computer Program for Applying Energy to an Object), filed Dec. 2, 2008 which are entering the U.S. national stage concurrently with this application.

FIELD OF THE INVENTION

The invention relates to an apparatus, a method and a computer program for applying energy to an object. The invention relates further to a combination element for combining multiple energy applying elements for applying energy to the object for use in the apparatus and a method for producing the apparatus.

BACKGROUND OF THE INVENTION

An apparatus for applying energy to an object is, for example, used in the field of interventional treatment of atrial fibrillation, wherein cardiac tissue is denaturized by thermal therapy. Radio Frequency energy is applied to the cardiac tissue using a catheter and thermal energy is generated due to resistive losses in the tissue of the myocardium. The heated muscle cells in the cardiac tissue die off and lose their biological function, which can be measured by an increase in the tissue impedance.

U.S. Pat. No. 5,830,209 discloses a laser catheter comprising multiple optical fibers for applying optical energy to the tissue of a heart. The optical fibers are arranged in a small circle at the distal end of the catheter and emit light substantially in the same direction such that they form a broad light spot on the surface of the tissue when the catheter is in contact with the tissue. In order to apply energy along a line on the tissue, the catheter has to be moved along the line, i.e. the optical energy has to be applied at different locations along the line, wherein in between the different locations the catheter has to be detached from the tissue, moved to a next location and again attached to the tissue.

This leads to an inaccurate application of optical energy to the tissue, in particular, if the object is moving.

SUMMARY OF THE INVENTION

It is an object of the present invention to provide an apparatus, a method and a computer program for applying energy to an object, which allow applying energy along a line more accurately. It is a further object of the present invention to provide a corresponding combination element comprising energy applying elements for use in the apparatus and a method for producing the apparatus.

In a first aspect of the present invention an apparatus for applying energy to an object is presented, wherein the apparatus comprises at least one combination element for combining multiple energy applying elements for applying energy to the object, wherein the combination element comprises an axis, around which the energy applying elements are wound, wherein the energy applying elements comprise energy emission locations arranged along a line.

The invention is based on the idea that, since the energy emission locations are arranged along a line, energy can be applied to the object along the line, wherein, since the energy applying elements comprising the energy emission locations are wound around the axis of the combination element, the multiple energy emission locations can be arranged very close to each other, i.e. the distance between neighboring locations of the object, to which energy is applied, is very small or there is no distance at all, i.e. energy could, for example, be applied along a continuous line. Furthermore, since energy can be applied along the line, while the energy emission locations are, for example, in contact with the object, without the need to move energy applying elements from one location to another location, the accuracy of applying energy along a line is improved.

The line, along which the energy emission locations are arranged, is preferentially parallel to the axis of the combination element. It is further preferred that the line is a substantially straight or curved line or that the line forms a helix. The line can also be a closed loop. Preferentially, the line extends in a longitudinal direction of the combination element.

The energy applying elements comprise, for example, optical fibers, if optical energy is to be applied, or electrical wires, if electrical energy is to be applied, wherein the optical fibers or the electrical wires, respectively, are wound around the axis of the combination element.

The energy emission locations are preferentially locations, at which the energy, for example, optical energy or electrical energy, leaves the energy applying element. For example, in the case of an optical fiber, the energy emission location is defined by the location, at which a cladding of the optical fiber and possible further coatings are removed from an optical fiber core such that light can leave the optical fiber. In the case of an electrical wire, which is preferentially surrounded by an insulating material, the energy emission location is the location, at which the insulating material is removed from the electrical wire such that electrical energy can leave the electrical wire.

The apparatus preferentially comprises a tube, in particular a catheter, in which the combination element and, thus, the energy applying elements, in particular optical fibers, are located for guiding the energy applying elements to the location, at which energy has to be applied, i.e., if the apparatus is used for, for example, an ablation procedure within a heart chamber, the energy applying elements are located within a guiding catheter for guiding the energy applying elements to the human heart.

The apparatus preferentially further comprises guiding means for steering and/or navigating the tube containing the combination element and, thus, the energy applying elements to the location, at which the energy has to be applied, in particular within an inner space of an object, like a heart chamber.

The energy applying elements are preferentially adapted for an optical ablation procedure applied to tissue of the object.

It is preferred that the combination element further comprises sensing elements for sensing the object, which are wound around the axis of the combination element, wherein the sensing elements comprise sensing locations arranged along the line, along which the energy emission locations are arranged. Thus, properties of the object, like the temperature or the electrical potential, can be sensed along a line, along which also energy is to be applied. This allows controlling the application of energy by monitoring the sensed properties of the object. The sensing elements comprise, for example, electrical wires for transferring electrical signals from the sensing locations to an electrical measuring device for measuring an electrical potential of the object, or optical fibers for transferring optical signals from the sensing locations to an optical measuring device, for example, a spectroscope, for determining properties like the absorption, scattering and/or reflection behavior optically. The electrical wires and/or the optical fibers are wound around the axis of the combination element. The sensing locations are preferentially locations, at which a signal, in particular an electrical or an optical signal, can be received and enter the sensing element, for example, enter the electrical wire or the optical fiber. For example, in the case of an optical fiber, the sensing location is defined by the location, at which a cladding of the optical fiber and possible further coatings are removed from an optical fiber core such that light can enter the optical fiber. In the case of an electrical wire, which is preferentially surrounded by an insulating material, the sensing location is the location, at which the insulating material is removed from the electrical wire such that an electrical signal can enter the electrical wire.

The sensing elements are, for example, adapted for temperature sensing or electrical sensing, wherein for a temperature sensing the sensing elements comprise preferentially thermocouples. The sensing elements are preferentially independent from each other. It is further preferred that each sensing element is assigned to an energy applying element such that for each location, at which energy is applied, a property of the object is independently sensed. It is further preferred that the energy applying elements are individually controllable. Furthermore, the sensing elements can comprise an optical temperature sensor, which comprises, for example, a phosphor coating at the end of an optical fiber.

It is further preferred that the energy application elements and the sensing elements are alternately wound around the axis such that at least some of the energy emission locations and some of the sensing locations are arranged alternately. By using this arrangement, energy emission locations and sensing locations are arranged close together, wherein the accuracy of the sensing of a property at a location, at which energy is applied, or close to this location, is improved.

The combination element preferentially comprises a holding element forming the axis. That is, the energy application elements and, if present, also the sensing elements, for example, optical fibers and/or electrical wires, are wound around the holding element. The holding element supports and/or guides the energy applying elements and the sensing elements, which are preferentially also present.

The holding element is preferentially a wire. It is also preferred that the holding element has a memory-shape effect such that it has a predetermined shape, if it is not in a forced shape, for example, because the holding element is inside a tube like a catheter, which keeps the holding element in a certain shape, for example, in a linear shape. This allows guiding the energy applying element to the locations, at which energy is to be applied, while the combination elements are in a linear shape within the tube, wherein the holding element can give the combination elements a predetermined shape for the application of energy, after the combination element has left the tube at the locations, at which energy is to be applied. The holding element is preferentially a memory metal alloy wire, in particular a nitinol wire.

The holding element is preferentially tubular. A tubular holding element has the effect that material can be transferred to or from the locations, at which the combination element is located, within the holding element, for example, from or to the outside of the object. For example, physiological saline solution can be transferred within the holding element for irrigating and cooling the location, at which energy is to be applied or has been applied. Preferentially the tubular holding element has holes along the axis of the combination element and the holes are preferentially not covered by, for example, the energy applying element, such that a material like physiological saline solution can leave or enter the tubular holding element along the axis. In particular, the energy applying elements can comprise optical fibers, in which holes are located, in order to allow a transmission of material from or to the hole of the tubular holding element. The holes can be arranged such that physiological saline solution, which leaves the holes, can act as an optical guiding for guiding light from optical fibers to the object and/or vice versa. The tubular holding element is preferentially a nitinol tube.

It is also preferred that a multiple of combination elements form an arrangement, in particular a basket structure, which is changeable between a folded condition, in which the multiple of combination elements are parallel to each other, and an unfolded condition, in which the multiple of combination elements are not parallel to each other, in particular, in which they need more space than in the folded condition and in which the optical fibers with the conductive coating are located on a surface of a volume, in particular an elliptical or spherical volume, defined by the combination elements. This allows guiding the combination elements to the locations, at which energy is to be applied, within a tube, while the combination elements are in the folded condition, wherein, after the locations, at which energy is to be applied, have been reached, the combination elements can leave the tube and can be transformed into the unfolded condition. Preferentially, in the unfolded condition the combination elements are in contact with a surface of the object for applying energy and preferentially sensing the object.

The combination element preferentially comprises a casing, in which the energy application elements are located. Preferentially, also the sensing elements and preferentially the holding element are located within the casing. The casing separates the inside of the casing, in particular the energy application elements, from the outside of casing, which is, for example, a heart chamber, in which blood is present. The casing is preferentially elastic such that the combination element can be shaped according to the shape of the holding element, in particular if the holding element has a memory effect. The casing is preferentially made of a biocompatible material. It is further preferred that the casing is adapted such that energy, in particular optical and/or electrical energy, can be exchanged between the inside and the outside of the casing, i.e. that the casing is at least partly optically transparent and/or electrically conductive.

It is further preferred that the casing comprises a window, which is at least partly transparent to energy of the energy applying element at the energy emission locations, in particular, the window is at least partly transparent to light and/or conductive for electrical energy. Preferentially, a material is transparent to electrical energy, i.e. electrically transparent, if the material is electrically conductive. This allows transmitting energy, for example, optical and/or electrical energy, between the inside and the outside of the casing. Preferentially micro-lenses for focusing and/or steering light can be added to the window, if the energy applying energy apply light. If optical energy is applied, it is further preferred that the window comprises spreading particles that preferentially do not absorb light, like $TiO_2$.

The window is preferentially at least partly optically transparent and at least partly electrically conductive. This allows transmitting light between the inside and the outside of the casing. The electrically conductive window or the electrically conductive part of the window is preferentially electrically in contact with an electrically conductor of the energy application elements or the sensing elements, which should receive or apply an electrical signal. This contact is preferentially located at a place, at which an electrical signal should be received or applied. The optically transparent part is preferentially not electrically conductive. This inhibits a transmission of an electrical signal from the object through the optically transparent part of the window, which could be the heart.

It is further preferred that the window or a multiple of windows is dimensioned in the longitudinal direction such that each energy applying element can apply energy through the window or through the multiple of windows. If the combination element further comprises sensing elements, the window or a multiple of windows is preferentially dimensioned in the longitudinal direction such that also sensing element can receive signals from the object through the window or through the multiple of windows.

The window preferentially comprises at least two kind of materials, an optically transparent material and an electrically conductive material, wherein the optically transparent material is located at locations, at which optical energy should be transmitted, and wherein the electrically conductive material is located at locations, at which the electrical energy should be transmitted. The electrically conductive window comprises preferentially titanium or platinum-iridium. The window is preferentially biocompatible.

It is further preferred that at least a part of the window is formed by a tube-shaped or ring-shaped material arranged around the casing and a position, at which an opening is located in the casing. This facilitates the manufacturing process of the combination element, because firstly the combination element with the casing has to be produced. Then, an opening can be made at a desired location with a desired size, and, after that, the tube-shaped or ring-shaped material can be arranged around the casing. The decision about the size and position of the window can be made in a late step within the manufacturing process. The material is preferentially at least partly optically and/or electrically transparent. Furthermore, the material comprises at least partly fixing elements for fixing the material at the desired position, i.e. the material can have elastic properties or can, for example, be glued to the casing.

The window preferentially comprises alternately optically transparent and electrically conductive parts. This allows applying optical or electrical energy at a location and sensing a property of the object electrically or optically very close to the location, at which the energy is applied. This improves the quality of monitoring a property of the object during the application of energy.

At least two combination elements are preferentially wound together. This increases the number of energy emission locations along the line.

In a further aspect of the present invention a combination element for combining multiple energy applying elements for applying energy to the object for use in an apparatus is presented, wherein the combination element comprises an axis, around which the energy applying elements are wound, wherein the energy applying elements comprise energy emission locations arranged along a line.

In a further aspect of the present invention a method for applying energy to an object is presented, wherein energy is applied along a line by using at least one combination element for combining multiple energy applying elements for applying energy to the object, wherein the combination element comprises an axis, around which the energy applying elements are wound, wherein the energy applying elements comprise energy emission locations arranged along a line.

In a further aspect of the present invention a method for producing the apparatus for applying energy is presented, wherein a combination element for combining multiple energy applying elements for applying energy to an object is produced by winding energy applying elements around an axis of the combination element and by producing energy emission locations at the energy applying elements such that the energy emission locations are arranged along a line.

In a further aspect of the present invention a computer program for applying energy to an object is presented, wherein the computer program comprises program code for causing a computer to carry out the method for applying energy, when the computer program is run on a computer and controlling the energy applying apparatus as defined in claim 1.

It shall be understood that preferred embodiments of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
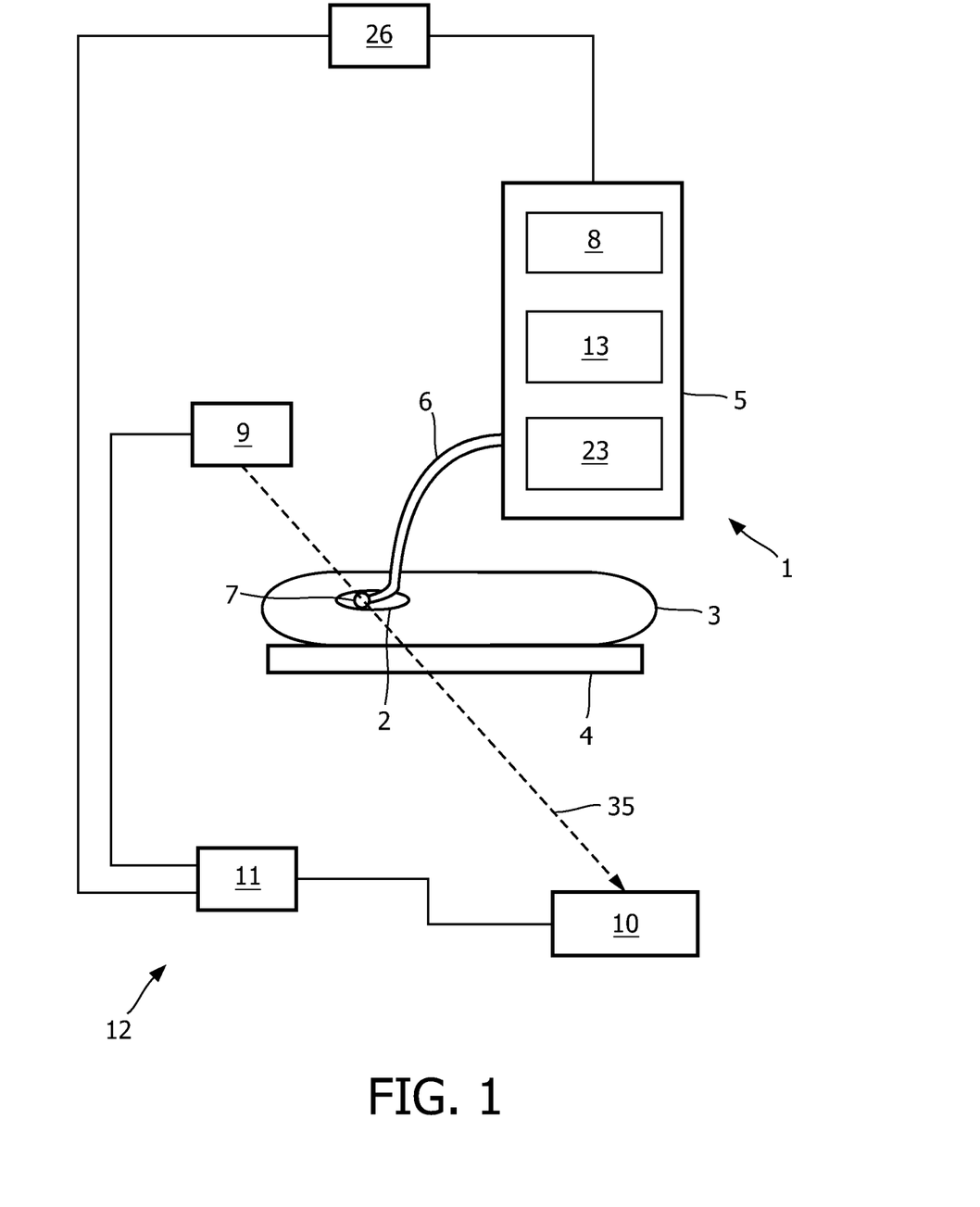
FIG. 1 shows schematically and exemplarily an apparatus for applying energy to an object in accordance with the invention.

FIG. 1 shows an apparatus 1 for applying energy to an object. The apparatus 1 comprises a tube, in this embodiment, a catheter 6, and an arrangement 7, which comprises energy emission locations and sensing locations. The arrangement 7 is connected to a first control unit 5 via the catheter 6. The catheter 6 with the arrangement 7 can be introduced into an object 2, which is, in this embodiment, a heart of a patient 3 located on a patient table 4, wherein the catheter 6 is steered and navigated to the heart chamber by build-in guiding means (not shown), which can be controlled from outside by a guiding control unit 23. In another embodiment, the catheter can, for example, be steered and navigated by using guiding wires to guide the catheter passively into the heart. Also the guiding wires can be controlled by the guiding control unit 23.

During introduction of the arrangement 7 and the catheter 6 into the object 2 an imaging device 12, which is in this embodiment, a fluoroscopy device, generates images of the object 2 and the arrangement 7. This imaging device 12 preferentially generates images of the object 2 and the arrangement 7, also if the arrangement 7 is already located within the object 2.

In other embodiment, the object can, for example, be another hollow organ of a patient or a technical object, in particular a hollow technical object, whose inner surface has to be treated with energy.

The imaging device 12, i.e. in this embodiment, the fluoroscopy device 12, comprises an X-ray source 9 and a detection unit 10, which are controlled by an imaging device control unit 11. The imaging device 12 generates X-ray projection images of the object 2 and of the arrangement 7 in a known way. The X-rays of the X-ray source 9 are schematically indicated by the arrow 35.

In another embodiment, instead of a fluoroscopy device, another imaging device can be used for generating an image comprising the object 2 and the arrangement 7. For example, a magnetic resonance imaging device, an ultrasonic imaging device or a computed tomography device can be used for generating an image of the object and the arrangement 7.

The first control unit 5 comprises the guiding control unit 23, an optical device 8 for applying optical energy and/or sensing and an electrical device 13 for applying electrical energy and/or sensing. The optical device 8 and/or the electrical device 13 are connected to energy applying elements for applying energy to the object. If optical energy has to be applied, the energy applying elements are optical fibers, which are connected to the optical device 8 and which transfer optical energy to the location within the object, at which the optical energy has to be applied. If electrical energy has to be applied to the object, the energy applying elements are electrical conductors, for example, electrical wires, which are connected to the electrical device and which transfer electrical energy to locations within the object, at which energy has to be applied. The energy applying elements are combined in a combination element, which comprises a multiple of energy applying elements, which are wound around an axis of the combination element, in particular, around a central axis of the combination element. The combination element further comprises sensing elements for sensing the object. The sensing elements comprise, for example, electrical wires for transferring sensed electrical energy from a sensing location to the electrical device 13. The sensing elements can be adapted, for example, for sensing the electrical potential of the object, for example, of the heart, and/or for sensing the temperature of the object. If the sensing elements are adapted for sensing the temperature of the object, the sensing elements are preferentially thermocouples. If an optical sensing should be performed, the sensing elements comprise optical fibers for transferring light from the sensing locations to the optical device. Also the sensing elements are wound around the axis of the combination element, i.e. the complete sensing elements or a part of the sensing elements are wound around the axis of the combination element. For example, if the sensing elements comprise electrical wires, the electrical wires are wound around the axis of the combination element, and, if the sensing elements comprise optical fibers, the optical fibers are wound around the axis of the combination element.

If the electrical device is used for sensing the object, the electrical device comprises preferentially a detector for measuring electrical signals for measuring, for example, the electrical potential or the temperature of the object. If the temperature of the object has to be measured, the sensing elements are preferentially thermocouples comprising two kinds of metallic material, which are contacted to each other at a sensing location, wherein a voltage between these two kinds of metallic material is measured by the electrical device and wherein the electrical device assigns a temperature to the measured voltage. The electrical device is preferentially adapted such that a property of the object can be measured at different sensing locations of the sensing elements individually. For example, the electrical device can comprise a single detector for each sensing element.

If the electrical device should be used for applying electrical energy, the electrical device preferentially comprises an electrical energy source, for example, a voltage source, which is connected to electrical wires for transferring the electrical energy to the locations, at which energy should be applied, in particular for transferring the electrical energy to energy emission locations of the energy applying elements. Preferentially, the different energy applying elements are individually addressable, i.e. for example, the electrical device comprises a dedicated circuit or several electrical energy sources, wherein each electrical energy source is connected to a single electrical wire of an energy applying element.

If the optical device should be used for an optical sensing, the optical device comprises preferentially an optical detector for measuring light and preferentially a spectroscope. In this case, the optical device is connected to the sensing elements, which are, for example, optical fibers, preferentially such that each sensing element is individually addressable, in order to sense properties of the object at different sensing locations independently from each other. The sensing elements preferentially measure light reflected or scattered by the object.

If the optical device should be used for applying optical energy, the optical device comprises, for example, at least one laser device, which is connected to an optical fiber being, in this embodiment, an energy applying element for transferring optical energy from the optical device to an energy emission location in the object. Preferentially, each energy emission location is addressable individually, i.e., for example, each energy applying element is connected to a single laser device of the optical device or the optical device comprises beam splitters, shutters or other optical elements for addressing the different energy applying elements individually.

In this embodiment, the electrical device is used for sensing and the optical device is used for applying optical energy.

Each energy applying element comprises a single energy emission location and each sensing element comprises a single sensing location. The energy emission locations and the sensing locations are substantially arranged along a line. This line extends preferentially in a longitudinal direction of the combination element and is preferentially parallel to the axis of the combination element, in particular, parallel to the central axis of the combination element. The line is preferentially a curved line, but the line can also be a straight line.

The energy emission locations are preferentially locations, at which the energy, for example, optical energy or electrical energy, leave the energy applying element. For example, in the case of an optical fiber, the energy emission location is defined by the location, at which a cladding of the optical fiber and possible further coatings are removed from an optical fiber core such the light can leave the optical fiber. In the case of an electrical wire, which is preferentially surrounded by an insulating material, the energy emission location is the location, at which the insulating material is removed from the electrical wire such that electrical energy can leave the electrical wire.

The arrangement 7 preferentially comprises a plurality of combination elements, which are located within the catheter 6, for guiding the combination elements and, thus, the energy applying elements and the sensing elements, to the location, at which energy has to be applied, i.e., if the apparatus 1 is used for, for example, an ablation procedure within a heart chamber, the combination elements are located within a catheter for guiding the combination elements to the human heart. Preferentially, the energy applying elements and the sensing elements are adapted for an optical ablation procedure applied to tissue of the object.

The energy application elements and the sensing elements are preferentially alternately wound around the object of the combination element such that at least some of the energy emission locations and some of the sensing locations are arranged alternately.

In this embodiment, the combination element comprises a holding element forming the axis, i.e. the electrical conductors, for example, wires, metallic foils or metallic coatings, and the optical fibers of the energy applying elements and the sensing elements are wound around the holding element. The holding element supports and guides the energy applying elements and the sensing elements and gives the combination element a particular shape. The holding element is, for example, a wire or a tube, which has a memory-shape effect such that it has a predetermined shape, if it is not in a forced shape, for example, because the holding element is inside the catheter 6, which keeps the holding element in a certain shape, for example, in a linear shape. This allows guiding the combination element comprising the energy applying elements and the sensing elements to the locations, at which energy is to be applied, while the combination elements are in a linear shape within a catheter 6, wherein the holding element can give the combination elements a predetermined shape for the application of the energy, after the combination element has left the catheter 6 at the locations, at which energy is to be applied. In this embodiment, the holding element is made of nitinol. If the holding element is a tube, the holding element preferentially comprises holes along the axis of the respective combination element, wherein the holes are not covered, by, for example, the energy applying elements or sensing elements, such that physiological saline solution can leave the tubular holding element along the axis. In particular, if the energy applying elements comprise optical fibers, holes can be located in the optical fibers, in order to allow a transmission of physiological saline solution from the hole of the tubular holding element. The holes can be arranged such that physiological saline solution, which leave the holes, can act as an optical guiding for guiding light from the respective optical fiber to the object and/or vice versa further.

The combination element comprises a casing, in which the energy applying elements and the sensing elements are located together with the holding element. The casing is, in this embodiment, elastic such that the combination element can be shaped according to the shape of the holding element. The casing is, in this embodiment, made of a biocompatible material and comprises, in this embodiment, a window, which is at least partly transparent to energy of the energy applying elements at the energy emission locations and at least partly transparent to a signal, which has to be sensed by the sensing elements, at the sensing locations.

In the following, different embodiments of a combination element are exemplarily shown.

Figure 2:
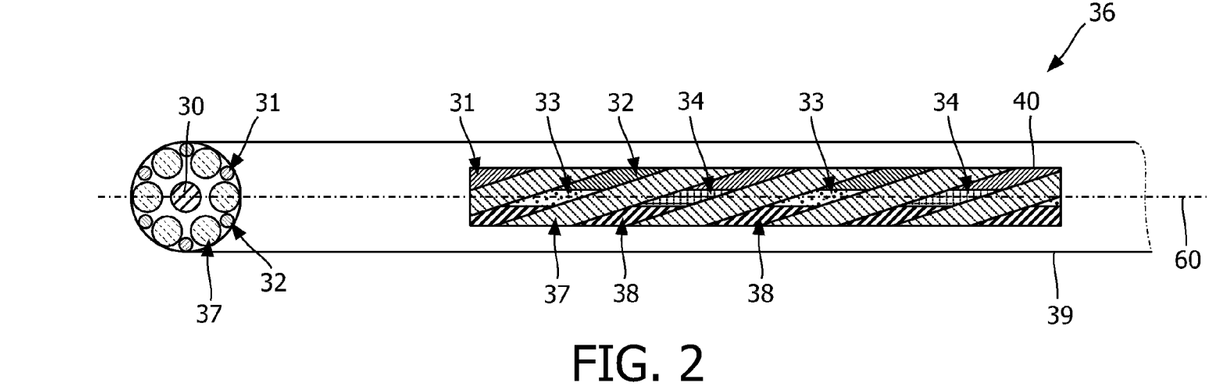
FIGS. 2 to 9 show schematically and exemplarily different embodiments of a combination element of a first type.

FIG. 2 shows schematically and exemplarily a combination element 36 comprising a holding element 30 being a nitinol tube. Electrical wires 31, 32 as sensing elements are wound around the holding element 30, i.e. around a central axis 60 of the combination element, together with optical fibers 37 as energy applying elements. The holding element 30, the electrical wires 31, 32 and the optical fibers 37 are located within a casing 39. The casing comprises a window 40, which is made at the side of the combination element 36. At the location of the window, a galvanic contact is made between the electrical wires 32 and the nitinol tube 30, in order to form a thermocouple for temperature sensing at the contact between the respective electrical wire 32 and the nitinol tube 30, wherein the locations of these contacts are temperature sensing locations. The temperature sensing locations are indicated by the reference signs 33. The electrical wires 31 are used for measuring the electrical potential of the object at the sensing locations 34. Since the electrical wires 31 are preferentially insulated, the insulation material is removed at the sensing locations 34. At an irrigation location 38 an opening to the nitinol tube is made, in order to irrigate, for example, points where a lesion of coagulated, denaturized tissue is planned. The window 40 is, in this embodiment, an opening, which is not covered by a material. In other embodiments, the opening can be covered by, for example, a cover, which is at least partly optically transparent and electrically transparent, i.e. electrically conductive, and which preferentially comprises holes for irrigation. That is, the cover preferentially comprises regions, which are optically transparent and preferentially electrically non-conductive, and regions, which are electrically conductive.

The nitinol tube 30 can comprise a metallic coating, wherein at the temperature sensing locations 33 the electrical wires 32 are contacted to this metallic coating for forming a thermocouple. The combination element 36 can be used for performing an irrigation, a multi-point application of energy, a multi-point temperature sensing and a multi-point electrical sensing simultaneously.

Figure 3:
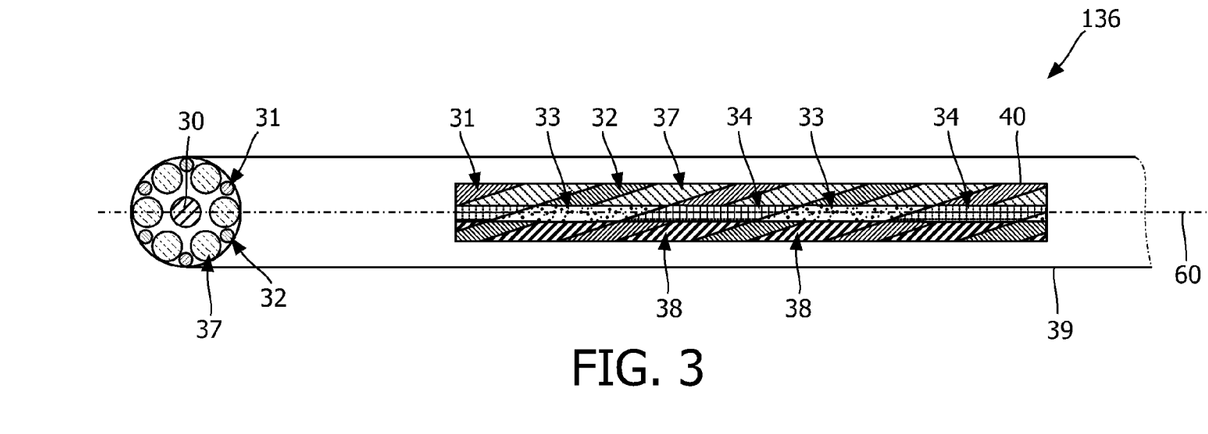

FIG. 3 shows schematically and exemplarily a further embodiment of a combination element 136. Similar elements in FIGS. 3 and 4 and also in the following figures comprise similar reference signs.

The combination elements 136 shown in FIG. 3 differs from the combination element 36 shown in FIG. 2 in that at the irrigation locations 38 a hole is made through the optical fibers 37. The inner part of this hole preferentially coated with a metal coating, which establishes a galvanic contact between an electric wire 32 and the holding element 30 or, if he holding element 30 comprises metallic coating, a contact between an electrical wire 32 and this coating, to form a thermocouple. Preferentially, the coating in the hole within the optical fibers is reflective for light, in particular, infrared light, in order to assist coupling of light from the optical fibers into the object, in particular, into the tissue of a human heart.

Figure 4:
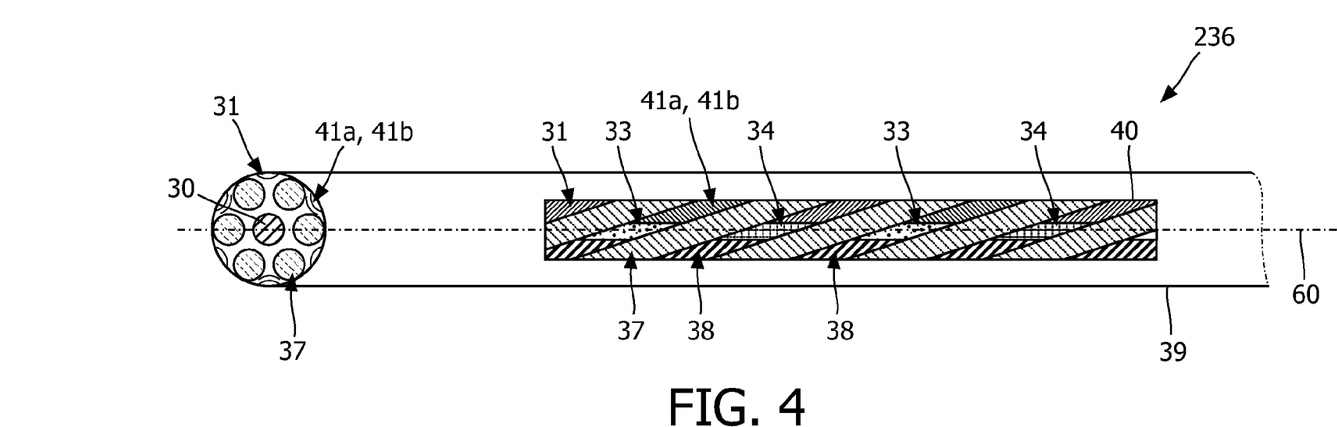

A further embodiment of a combination element is schematically and exemplarily shown in FIG. 4.

Figure 5:
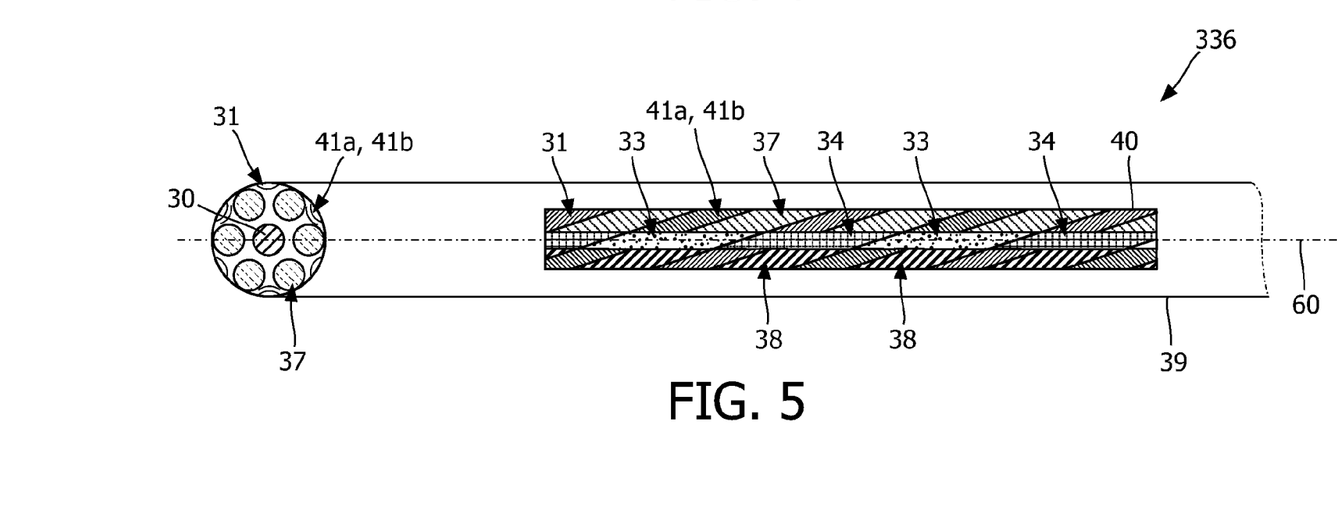

FIG. 4 shows a combination element 236 comprising two types of metallic foils 41a, 41b, which are used as sensing elements for a temperature sensing. The foils 41a, 41b are electrically insulated to each other except for the temperature sensing location 33, at which the two foils 41a, 41b are contacted for forming a thermocouple. The combination element 236 comprises several pairs of the two foils 41, 41b for providing several sensing elements with several temperature sensing locations 33. At the sensing location 34 electrical potentials can be measured using further metal foils 31. Irrigation openings 38 are made between optical fibers 37. In addition or alternatively, irrigation openings can be made in the optical fibers 37 and these irrigation openings can be coated, in order to make thermocouples and/or in order to support coupling light into the object, as explained above with reference to the combination element 136. Such an embodiment 336 of a combination element comprising the pairs of metal foils 41a, 41b and comprising irrigation holes 38 through the optical fibers 37 is exemplarily and schematically shown in FIG. 5.

Figure 6:
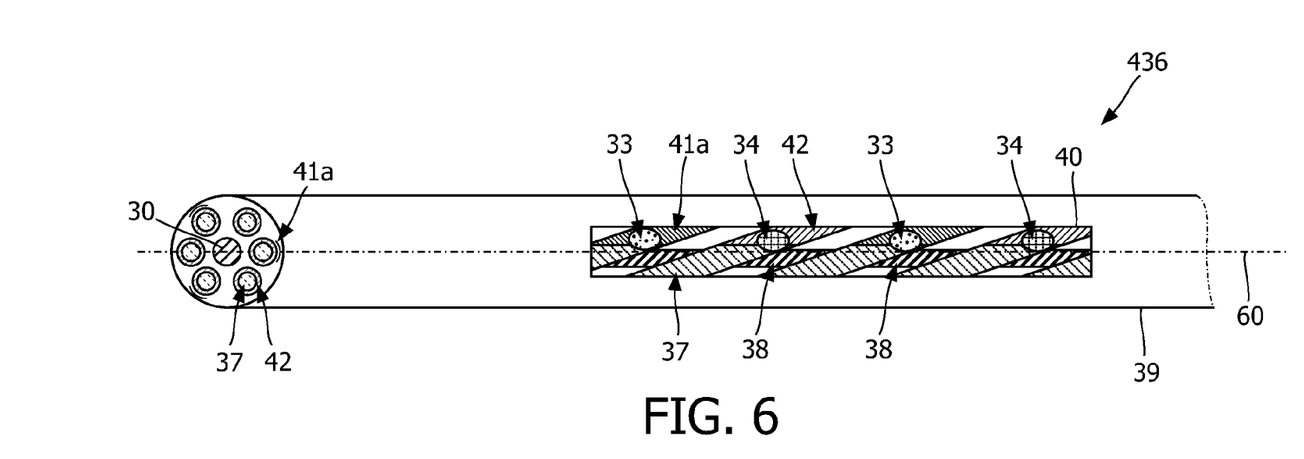

FIG. 6 shows schematically and exemplarily a further embodiment 436 of a combination element. The combination element 436 comprises several optical fibers 37 as energy applying elements, which are coated with a metal coating 42. As a sensing element or a part of a sensing element at least to some of the optical fibers 37, in particular to each optical fiber 37 a metallic foil 41a is added, wherein the metal coating 42 is electrically insulated with respect to the metal foil 41a. At the temperature sensing locations 33 a galvanic contact is made between the metal foil 41a and the metal coating 42. The galvanic contacts generate thermocouples for measuring the temperature. In another embodiment at the temperature sensing locations a thermocouple is created by coating each or at least some of the optical fibers with at least two metal coatings with an electrical insulation coating layer between them. At the temperature sensing locations a galvanic contact is made between the two metal coating layers for making the thermocouple. Furthermore, a metal coating on an optical fiber or on a holding element can be used for forming an electrical conductor for sensing electrical potentials of the object, in particular, in a human heart. In the embodiment 436 shown in FIG. 6, irrigation openings 38 are present in the tubular holding element 30 for irrigating the location, at which the optical energy is applied, in particular, for irrigation lesion locations.

Figure 7:
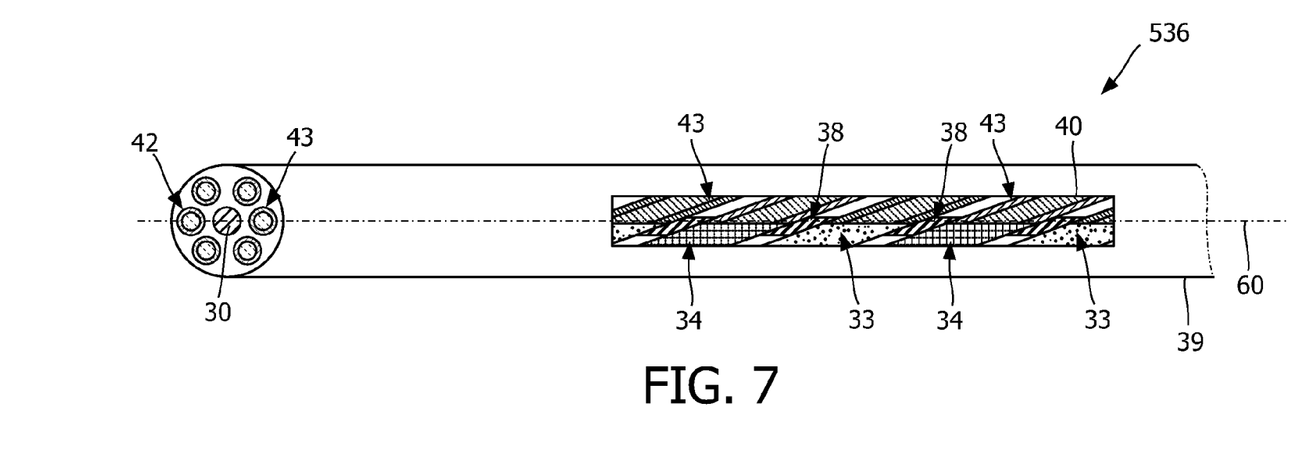

A further embodiment 536 of a combination element is exemplarily and schematically shown in FIG. 7. The combination element 536 comprises optical fibers 37, which are coated with a metal coating 42, 43. At the location of the window 40 a galvanic contact is made between the metal coating 43 and the holding element 30 or between the metal coating 43 and a metal coating on the holding element 30 at temperature sensing locations 33 for forming a thermocouple. At electrical sensing locations 34 electrical signals of the object are received using the metal coatings 42 of the optical fibers 37. An irrigation opening to the tubular holding element 30 is arranged at the irrigation locations 38. The temperature sensing locations are located close to the energy emission locations, at which light leaves the optical fibers.

Figure 8:
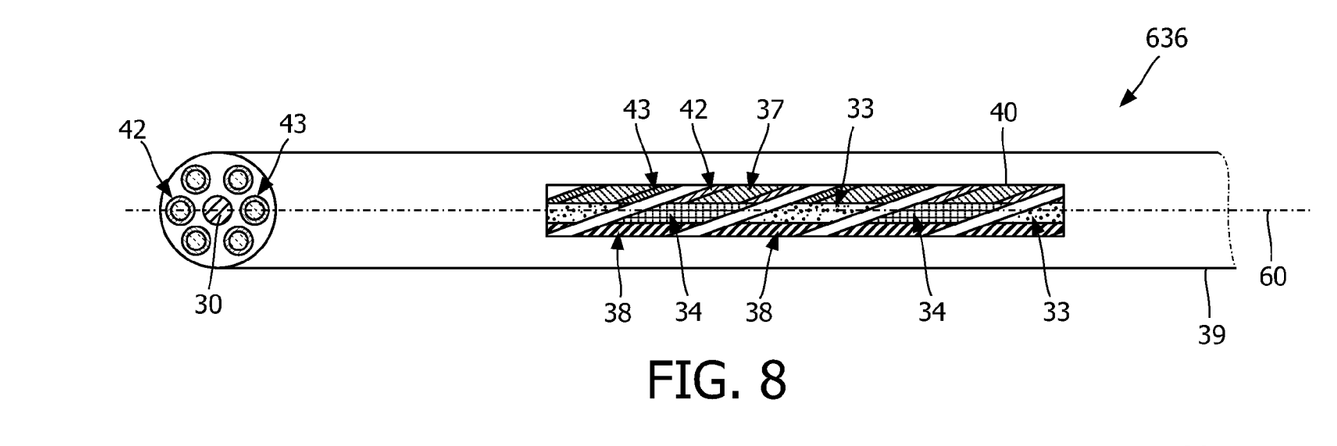

An embodiment 636, which is similar to the embodiment 536 shown in FIG. 7, is schematically and exemplarily shown in FIG. 8. The combination element 636 shown in FIG. 8 comprises irrigation openings located at irrigation locations 38 through the optical fibers 37. The inner part of the irrigation openings is coated with a metal coating, which preferentially establishes a galvanic contact between a metal coating 43 and the holding element 30 or between a metal coating 43 and a metal coating on the holding element 30 at the temperature sensing locations 33 for establishing a thermocouple. The metal coating in the irrigation opening is preferably reflective for light, in particular, for infrared light, for assisting coupling light from the optical fibers into the object, in particular, into the tissue of a human heart.

Figure 9:
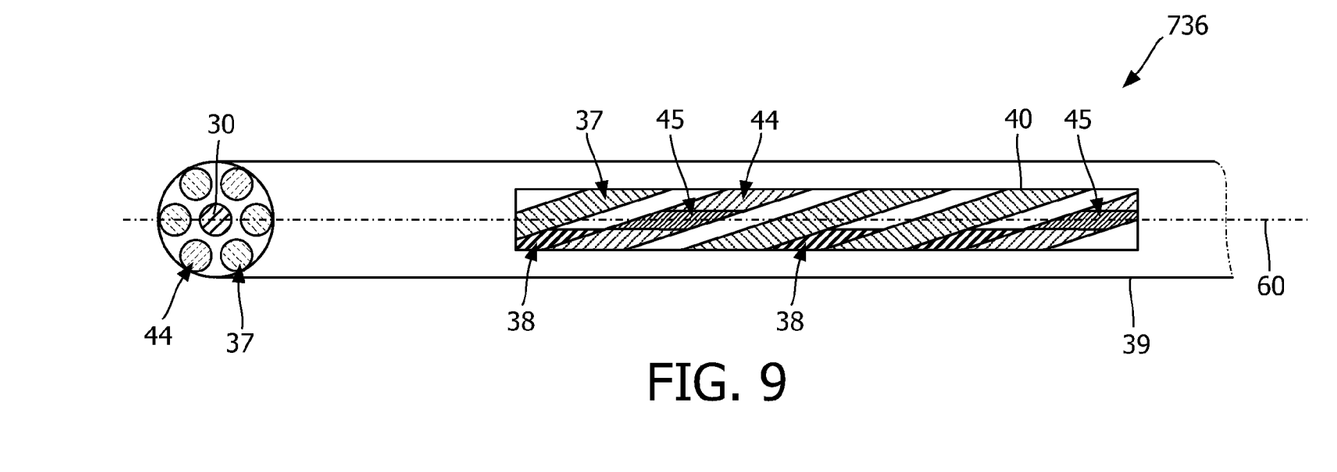

A further embodiment 736 of a combination element is schematically and exemplarily shown in FIG. 9. The combination element 736 uses, instead of or in addition to thermocouples, optical temperature sensors for sensing the temperature at the temperature sensing locations. In this case, the sensing elements comprise optical fibers 44, which comprise a phosphor coating 45. Also this combination element 736 can comprise further energy application elements and/or sensing elements, which are not shown in FIG. 9. Also the combination element 736 comprises irrigation openings 38.

In a preferred embodiment, several combination elements are wound together around a common axis and form a second type of combination element, which comprises several combination elements, which are described above and which can be regarded as combination elements of a first type. The second type combination element can comprise several first type combination elements without a casing. Preferentially, the second type combination element comprises a casing, in which the first type combination elements without a casing are located. The casing of the second type combination element preferentially comprises a window, which might be a simple opening in the casing with or without a cover and which allows the energy applying elements applying energy through the window at the energy emission locations and the sensing elements sensing the object at the sensing locations through the window. The second type combination element can comprise several windows. In another embodiment each first type combination element can comprise a casing, wherein the second type combination element does not comprise a casing.

Figure 10:
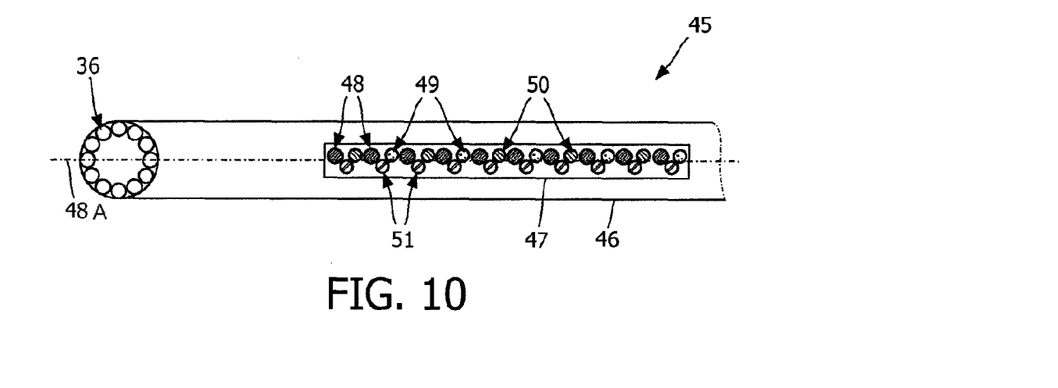
FIG. 10 shows schematically and exemplarily an embodiment of a combination element of a second type.

A second type combination element is exemplarily and schematically shown in FIG. 10. A second type combination element 45 comprises a casing 46 with a window 47. Several first type combination elements, in this embodiment, first type combination elements 36, are wound around a common axis 48A. Through the window 47 the energy applying elements and the sensing elements of the first type combination elements 36 are accessible. Furthermore, the tubular holding element of the first type combination elements 36 is accessible through the window 47. The energy emission locations of the energy applying elements, the sensing locations of the sensing elements and the irrigation locations of the tubular holding element are arranged along a line which is parallel to the axis 48A. FIG. 10 shows schematically energy emission locations 48, which emit optical energy and which are made by removing a cladding and possible further coatings of optical fibers at these locations, temperature sensing locations 49, which are preferentially made by galvanically contacting two metal types at these locations, electrical sensing locations 50 for sensing the electrical potential of the object and irrigation openings 51.

As already mentioned above, preferentially energy can be applied to the object at the different energy emission locations individually and independently from each other. Furthermore, preferentially properties of the object can be sensed at the different sensing locations independently from each other. It is further preferred, that the application of energy and the sensing of properties of the object is performed simultaneously. Thus, the application of energy can be controlled by sensing the properties of the object, like the electrical potential or the temperature, at the different sensing locations. The apparatus 1 further comprises a second control unit 26 for controlling the application of energy at the different energy emission locations in dependence on the sensed property at the different sensing locations, preferentially such that the sensed property at the different sensing locations does not exceed a predetermined threshold. The second control unit 26 is preferentially further adapted for controlling the imaging device 12.

The combination elements shown in FIGS. 2 to 9 are shown such that the left side of the combination elements is open. The left open side is only shown for illustrating the arrangement of elements within the optical fiber and within the combination elements, but, in real, the left sides shown in FIGS. 2 to 9 are closed such that preferentially all light energy is reflected, and is also coated with an electrical insulating material. The right hand side shown in FIGS. 2 to 9 is preferentially connected, in particular, plugged in, to the optical device and the electrical device.

The casing shown in FIGS. 2 to 9 can be a coating. Furthermore, the energy applying elements and possible sensing elements can be directly wound around the holding element, preferentially if they comprise an outer insulating coating or if they are not electrically conductive, or with a distance to the holding element. In the latter case, spacers can be arranged in between or the casing can comprise lumen, which are generally separated from each other and in which the energy application element and possible sensing elements are located, and which are in connection, where required for forming energy emission and/or sensing locations.

Figure 11:
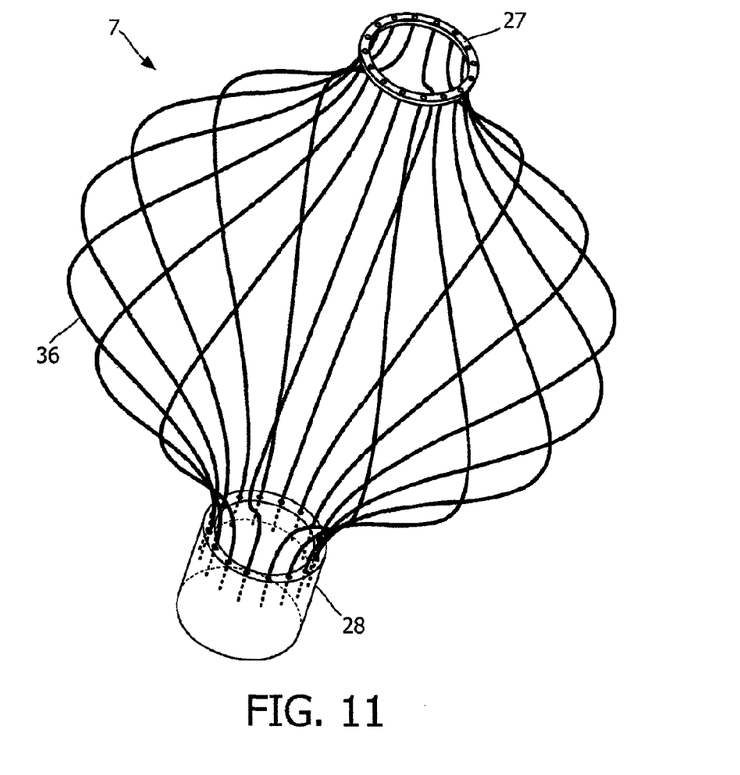
FIG. 11 shows schematically and exemplarily an arrangement of combination elements.

FIG. 11 shows schematically and exemplarily the arrangement 7, along which energy emission locations and sensing location are arranged. The arrangement 7 comprises several combination elements, in this embodiment, the combination elements 36. In other embodiments, the arrangement can comprise other combination elements, for example, the combination elements described above, first type and/or second type combination elements.

A multiple of combination elements 36 forms the arrangement 7, which is changeable between a folded condition, in which the multiple of combination elements 36 are parallel to each other, and an unfolded condition, which is shown in FIG. 11 and in which the multiple of combination elements 31 are not parallel to each other and in which the windows of the combination elements 36 are preferentially located on a surface of a volume, in particular, of an elliptical or spherical volume, defined by the combination elements 36. This allows guiding the combination elements 36 to the locations, at which energy is to be applied, within the catheter 6, while the combination elements 36 are in the folded condition, wherein, after the locations, at which energy is to be applied, have been reached, the combination elements 36 can leave the catheter 6 and can be transformed into the unfolded condition shown in FIG. 11. The catheter 6 and the arrangement 7 are, in this embodiment, guided such that at least some of the windows of the combination elements 36 are in contact with a surface of the object for applying energy to the object and sensing the object.

One end of the combination elements 36 is attached to ring element 37 and the other end of the combination elements 36 is attached to a shaft 28. Instead of the ring element 27, another element can be used, which fixes all combination elements 36 one to another. For example, a cap like structure can be used.

Figure 12:
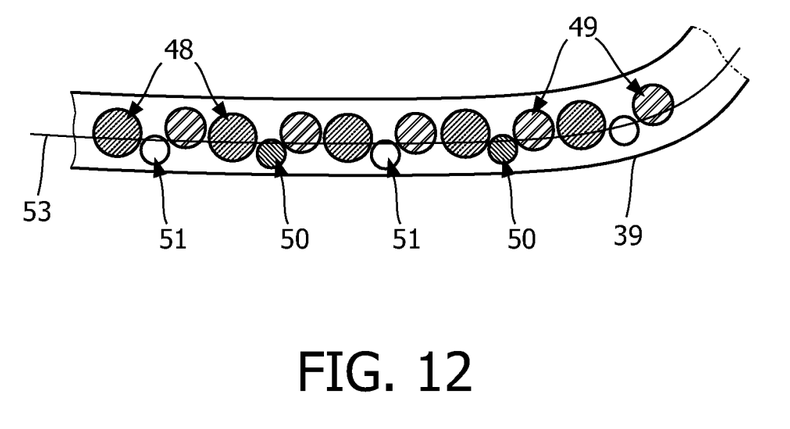
FIG. 12 shows schematically and exemplarily a distal end of a combination element.

FIG. 12 shows schematically and exemplarily a distal end of a combination element, in particular one of the first or second type combination elements described above, which comprises energy applying elements, sensing elements and a tubular holding element for irrigation. These elements are located in the casing 39, 46 of the combination element, which comprises a window, which is not shown in FIG. 12, wherein the energy applying elements, for example, optical fibers, and the sensing elements, for example, electrical wires, are wound around the holding element, which is, for example, a nitinol tube. As can be seen in FIG. 12, energy emission locations 48, temperature sensing location 49, electrical sensing locations 50 and irrigation openings 51 are arranged along a line 53. This allows the application of energy along a line, wherein the properties of the object can be sensed along this line and a cooling and irrigation can be performed along this line.

Figure 13:
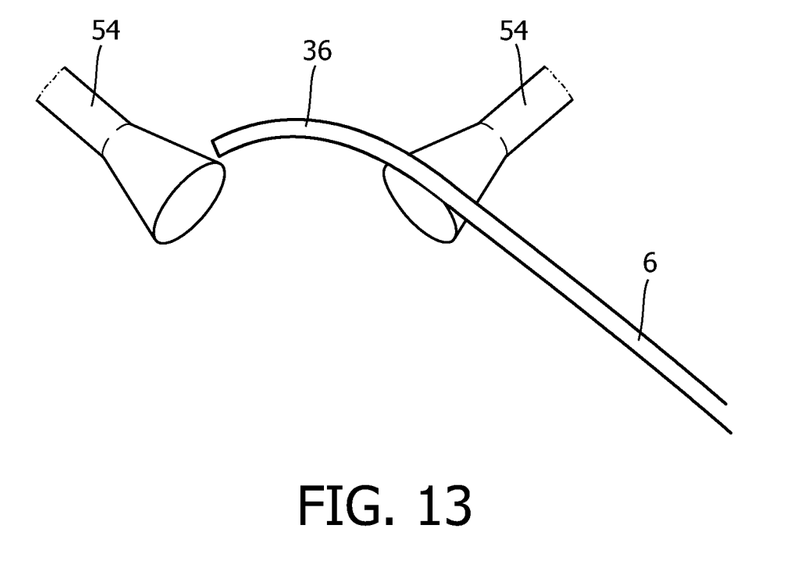
FIGS. 13 and 14 show schematically a combination element with a catheter arranged between two openings of pulmonary veins.

FIG. 13 shows schematically the catheter 6 of another apparatus for applying energy to an object, which comprises only one combination element 36. In other embodiments, the apparatus for applying energy to an object can comprise another single first type combination element, in particular, one of the first type combination elements illustrated above, or a second type combination element instead of the first type combination element 36 shown in FIG. 13. In FIG. 13, the combination element 36 is located between two openings 54 of pulmonary veins for applying energy along a line between these two openings 54.

Figure 14:
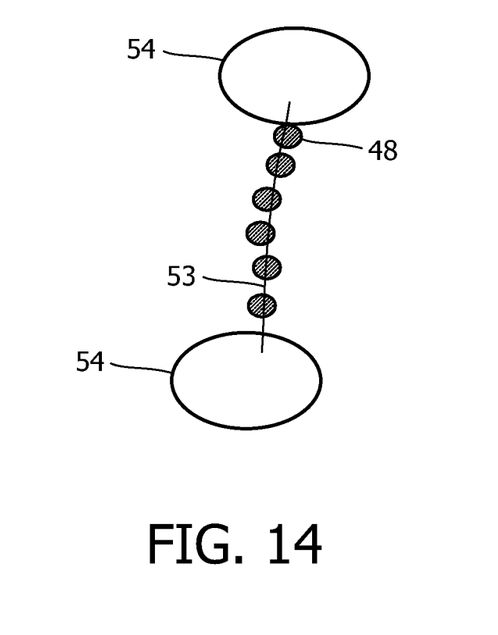

The arrangement of the energy emission locations 48 is schematically and exemplarily shown in FIG. 14. The energy emission locations 48 are arranged along the line 53 between the two openings 54 of pulmonary veins for producing a linear lesion between these two openings.

Figure 15:
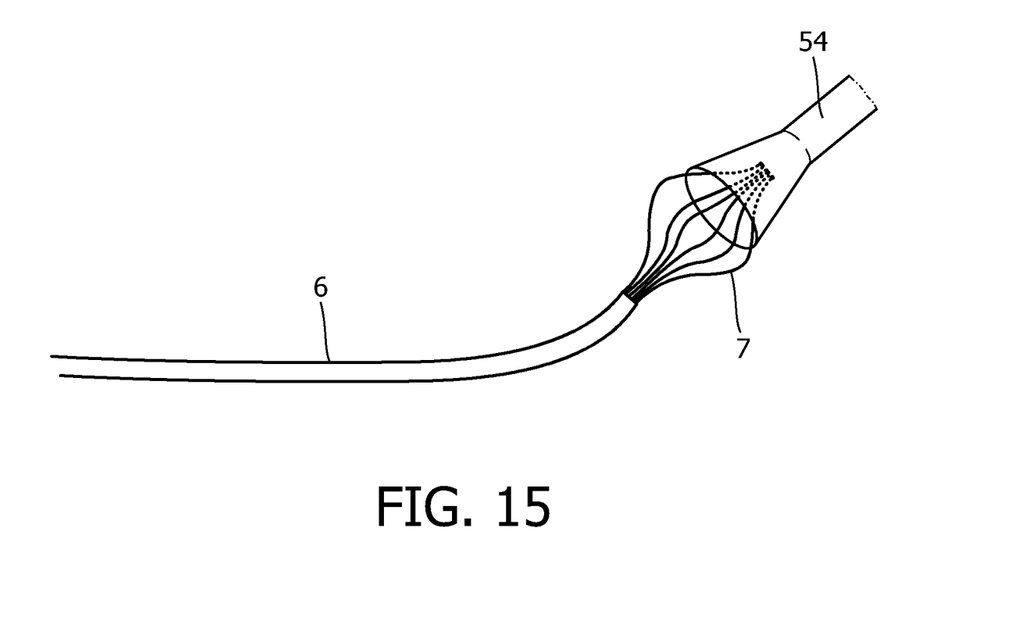
FIGS. 15 and 16 show schematically and exemplarily an arrangement of combination elements at an opening of a pulmonary vein.

FIG. 15 shows schematically and exemplarily a location of the arrangement 7 of the apparatus 1 for applying energy to an object, which is shown in FIG. 1. In FIG. 15, the arrangement 7 is unfolded and is in contact with an opening 54 of a pulmonary vein. The arrangement of the energy emission locations 48 is schematically and exemplarily shown in FIG. 16. The energy emission locations 48 are arranged along a closed line 55, which encloses the opening 54 of the pulmonary vein.

Figure 16:
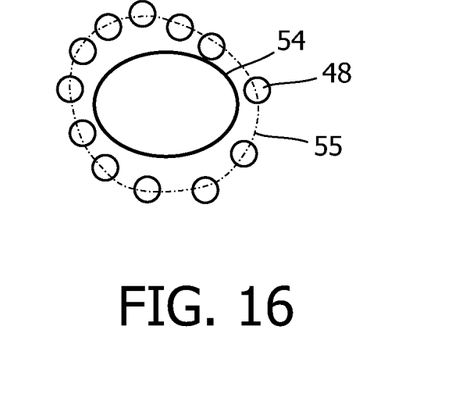

The catheter is preferentially dimensioned such that it can be guided through a standard guiding catheter. The catheter has therefore an outer diameter which is preferentially smaller than 3 mm, if the arrangement 7 is in the folded condition. If the arrangement 7 is in the unfolded condition and, for example, pressed again an opening 54 of a pulmonary vein as schematically shown in FIGS. 15 and 16, the diameter of the closed line 55 is preferentially minimally about 15 or 16 mm. Furthermore, the distance between the centers of two neighbored energy emission locations 48 is preferentially smaller than 5 mm for performing an ablation procedure around an opening of the pulmonary vein. In particular, the distance between two neighbored energy emission locations 48 is preferentially 4 mm. For example, 12 optical fibers can be present within a casing of a combination element, wherein the outer diameter of the optical fibers can be 100 µm. The outer diameter of the irrigation tube can be 300 µm. A combination element can therefore have an outer diameter of, for example, 500 to 600 µm. Preferentially, the arrangement 7 can comprise 10 to 15 combination elements, from the first type or from the second type. Electrical wires have preferentially a diameter smaller than 25 µm and can therefore be integrated within the casing of a combination element without increasing its outer diameter.

Figure 17:
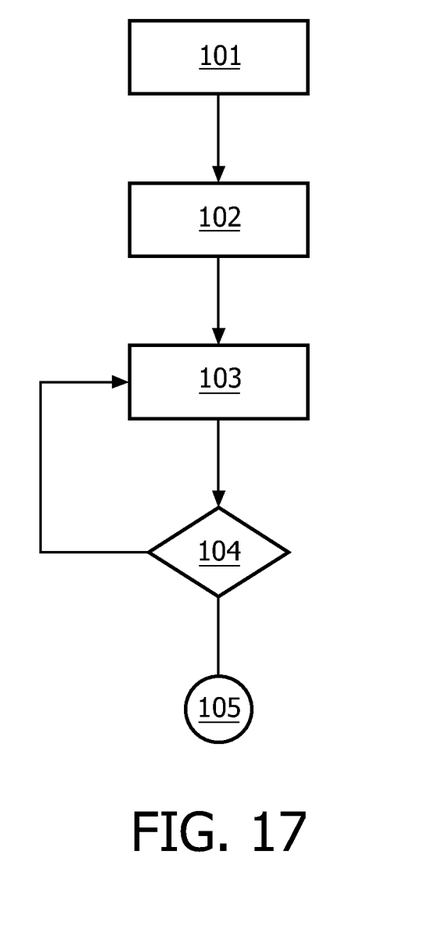
FIG. 17 shows a flow chart exemplarily illustrating a method for applying energy to an object.

In the following a method for applying energy to an object will be explained with reference to a flow chart shown in FIG. 17.

In step 101, the arrangement 7 is in the folded condition and located within the catheter 6 and the catheter 6 is guided to a desired location within the object by using the guiding control unit 23.

In step 102, by using the guiding control unit 23 the arrangement 7 leaves the catheter 6 and is transformed into the unfolded condition, which is schematically shown in FIG. 11. The unfolded arrangement 7, which now has a basket structure, is guided such that it is in contact with the locations of the object 2, to which energy should be applied. Since the arrangement 7 comprises several energy emission locations and several sensing locations, a multi-point energy application and sensing can be performed. In another embodiment, instead of the arrangement 7, another arrangement of combination elements or a single combination element of the first type or of the second type can be used.

At least some of the energy emission locations and at least some of the sensing locations are in contact with the object, wherein the contact force is sufficiently large that the energy emission locations and the sensing locations do not move with respect to a surface of the object, on which they are located, even if the object is moving.

In step 103, the optical device 8 applies optical energy via the optical fibers at a plurality of energy emission locations and simultaneously the object is sensed at the sensing locations by the sensing elements, in order to monitor the application of optical energy. Preferentially, simultaneously the locations of the object, at which energy is applied, are cooled and irrigated by physiological saline solution leaving the irrigation openings.

The application of energy and the monitoring is controlled by the second control unit 26 and, if the second control unit 26 detects that the sensed properties of the object are outside a predefined range, the second control unit 26 decides in step 104 that the application of the energy has to be stopped in step 105. Also if a user inputs into the second control unit 26, that the application of energy has to be stopped, the second control unit 26 stops the application of energy.

The guiding of the catheter 6 with the arrangement 7 within the object 2 is monitored by the imaging device 12.

Figure 18:
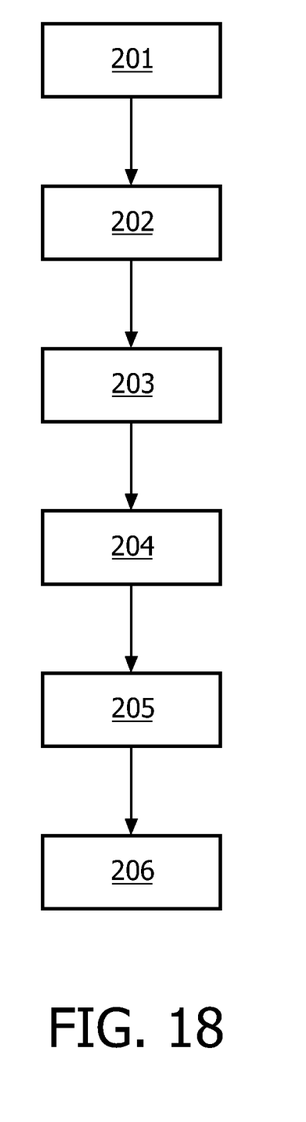
FIG. 18 shows a flow chart exemplarily illustrating a method for producing an apparatus for applying energy to an object.

In the following a method for producing an apparatus for applying energy will exemplarily explained with reference to a flow chart shown in FIG. 18.

In step 201, several energy applying elements and several sensing elements, in particular, several optical fibers and several electrical wires, are provided. Furthermore, holding elements, in particular, preshaped nitinol tubes are provided.

In step 202, at least one combination element, which combines several energy applying elements and sensing elements, is produced by winding several energy applying elements and several sensing elements around a holding element. In this embodiment, several optical fibers and several electrical wires are wound around a nitinol tube, which serves as a holding element.

In step 203, energy emission locations and sensing locations are produced at the energy applying elements and the sensing elements. In another embodiment, step 203 can be performed before step 202. In this embodiment, a cladding and possible further coatings are removed from the optical fiber core at the energy emission location such that light can leave the optical fiber core and can be applied to the object. Furthermore, in this embodiment, each electrical wire comprises an insulating coating, which is removed at the respective sensing location.

In step 204, a casing is added to each combination element such that each combination element comprises a casing, in which the energy applying elements and the sensing elements are located. In this embodiment, the nitinol tube with the wound optical fibers and electrical wires is located in the casing. The casing comprises at least one window, wherein the holding element with the energy applying elements and the sensing elements is arranged within the casing such that the energy emission locations and the sensing locations are located at the window.

After a multiple of combination elements has been produced, these combination elements are combined to the arrangement 7 such that the combination elements form a basket structure, if the combination elements are free, i.e. if there are not in a forced-shape, because, for example, there are located within a catheter 6.

In step 206, the arrangement 7 is located within a catheter 6 such that the arrangement 7 can be moved out of the catheter 6 and back into the catheter 6. Furthermore, the energy applying elements and/or the sensing elements are connected to the optical device 8 and the electrical device 13. In particular, the optical fibers are connected to the optical device 8 and the electrical wires are connected to the electrical device 13. Furthermore, the optical device 8, the electrical device 13 and a guiding control unit 23 are combined to a first control unit 5, which is connected to a second control unit 26, wherein the second control unit 26 is connected to an imaging device 12.

In the above described embodiments, energy is applied to tissue of a human heart and the properties of this tissue are sensed. In other embodiments, energy can be applied to another object, for example, a technical object, and the properties of the technical object can be sensed by the sensing elements.

In the above described embodiment, optical energy is applied to the object and the object is electrically sensed. In another embodiment, electrical energy can be applied to the object using the electrical device and electrical conductors, like electrical wires, metal foils or metal coatings, and the object can be optically sensed using the optical device and the optical fibers. In this case, the electrical device preferentially comprises a plurality of electrical energy sources and the optical device comprises preferentially a spectroscope.

The combination elements schematically and exemplarily shown in FIGS. 2 to 10 are preferred embodiments only and do not limit the scope of the invention, in particular, the distribution of the different wires, foils, coatings and optical fibers and of the temperature sensing, electrical sensing and irrigation location are schematically and exemplary shown and should not limit the scope of the invention.

The apparatus for applying energy to an object can be used, for example, for a circumferential ablation and/or a segmental ablation.

While the invention has been illustrated and described in detail in the drawings and foregoing description such illustration and description are to be considered illustrative or exemplarily and not restrictive. The invention is not limited to the disclosed embodiments.

Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for applying energy to an object, the apparatus comprising:
at least one combination element for combining multiple energy applying elements for applying energy to the object, wherein the energy applying elements are wound around an axis of the combination element, wherein the energy applying elements comprise energy emission locations arranged along a line; and sensing elements for sensing the object, wherein the sensing elements are wound around the axis of the combination element, wherein the sensing elements comprise sensing locations arranged along the line along which the energy emission locations are arranged, and wherein the energy application elements and the sensing elements are alternately wound around the axis such that at least some of the energy emission locations and some of the sensing locations are arranged alternately wherein at least one of the energy application elements and the sensing elements is completely wound around the axis, wherein the combination element comprises irrigation openings, and wherein an inner part of the irrigation opening is coated with a metal coating.

2. The apparatus as defined in claim 1, wherein the combination element comprises a holding element forming the axis, and wherein the holding element comprises a metallic coating.

3. The apparatus as defined in claim 2, wherein the holding element is tubular.

4. The apparatus as defined in claim 1, wherein the combination element comprises a casing in which the energy application elements are located.

5. The apparatus as defined in claim 4, wherein the casing comprises a window which is at least partly transparent to energy of the energy applying element at the energy emission locations.

6. The apparatus as defined in claim 1, wherein at least two combination elements are wound together.

7. A combination element for combining multiple energy applying elements for applying energy to the object for use in the apparatus as defined in claim 1.

8. The apparatus of claim 1, wherein the line extends in a longitudinal direction of the combination element.

9. The apparatus of claim 1, wherein the axis is a central axis of the combination element, and wherein the line is parallel to the central axis.

10. The apparatus of claim 1, wherein the line is a curved line.

11. The apparatus of claim 1, wherein the line is a straight line.

12. A method for applying energy to an object comprising the acts of:
winding energy applying elements around an axis of a combination element;
applying energy along a line by using the energy applying elements wound around the axis for applying energy to the object, wherein the energy applying elements comprise energy emission locations arranged along the line; and
sensing the object using sensing elements, wherein the sensing elements are wound around the axis of the combination element, wherein the sensing elements comprise sensing locations arranged along the line along which the energy emission locations are arranged, and wherein the energy application elements and the sensing elements are alternately wound around the axis such that at least some of the energy emission locations and some of the sensing locations are arranged alternately wherein at least one of the energy application elements and the sensing elements is completely wound around the axis, wherein the combination element comprises irrigation opening, and wherein an inner part of he irritation openings is coated with a metal coating.

13. The method of claim 12, wherein the line extends in a longitudinal direction of the combination element.

14. The method of claim 12, wherein the axis is a central axis of the combination element, and wherein the line is parallel to the central axis.

15. The method of claim 12, wherein the line is a curved line.

16. The method of claim 12, wherein the line is a straight line.

17. The method of claim 12, wherein the combination element comprises a holding element forming the axis, and wherein the holding element comprises a metallic coating.

18. A non-transitory computer readable medium embodying computer instructions which, when executed by a processor, configure the processor to perform the acts of:
winding energy applying elements around an axis of a combination element, the combination element comprising irrigation openings, an inner irrigation openings being coated with a metal coating;
applying energy along a line by using the energy applying elements wound around the axis for applying energy to an object, wherein the energy applying elements comprise energy emission locations arranged along the line; and
sensing the object using sensing elements, wherein the sensing elements are wound around the axis of the combination element, wherein the sensing elements comprise sensing locations arranged along the line along which the energy emission locations are arranged, and wherein the energy application elements and the sensing elements are alternately wound around the axis such that at least some of the energy emission locations and some of the sensing locations are arranged alternately, wherein at least one of the energy application elements and the sensing elements is completely wound around the axis.

* * * * *